United States Patent
Ehlert et al.

(10) Patent No.: US 6,362,487 B1
(45) Date of Patent: Mar. 26, 2002

(54) METHOD AND DEVICE FOR NONDESTRUCTIVE DETECTION OF CRYSTAL DEFECTS

(75) Inventors: Andreas Ehlert, Mehring; Michael Kerstan, Burghausen; Holger Lundt, Burghausen; Dieter Helmreich, Burghausen, all of (DE)

(73) Assignee: Wacker Siltronic Gesellschaft für Halbleitermaterialien AG, Burghausen (DE)

( * ) Notice: Subject to any disclaimer, the term of this patent is extended or adjusted under 35 U.S.C. 154(b) by 0 days.

(21) Appl. No.: 09/318,655

(22) Filed: May 25, 1999

(30) Foreign Application Priority Data

Jun. 18, 1998 (DE) .......................... 198 27 202

(51) Int. Cl.$^7$ .............................. G01N 21/64
(52) U.S. Cl. .................. 250/458.1; 250/459.1; 356/73
(58) Field of Search .................. 250/458.1, 459.1, 250/484.5; 356/73, 237.1

(56) References Cited

U.S. PATENT DOCUMENTS 4,448,525 A * 5/1984 Mikoshiba et al. ........... 356/73
5,371,588 A * 12/1994 Davis et al. .................. 356/349
5,377,006 A   12/1994 Nakata
5,781,294 A *  7/1998 Nakata et al. ................ 356/349
5,936,726 A *  8/1999 Takeda et al. ............. 356/237.2

FOREIGN PATENT DOCUMENTS

EP         0735378        10/1996

OTHER PUBLICATIONS

VLSI Electronics, Microstructure Science vol. 12, Silicon Materials Academic Press, 1985.
J. Appl. Phys. 30, (1959) 163.
H. Jundt, M. Kerstan & R. Weiss, Proc. of the Spring Topical Meeting of the Amer. Soc. for Precision Engineering.
Abstract of English Corresponding to EP 0 735 378.
The Nomanclature for Crystal Defects is in Accord. with the Standards from DIN. DIN 50434.
ASTM (American Society for Testing Materials) FR4N–93, D93–3141, F–84–28, F416–75, F 416–88.

* cited by examiner

Primary Examiner—Constantine Hannaher
Assistant Examiner—Otilia Gabor
(74) Attorney, Agent, or Firm—Collard & Roe, P.C.

(57) ABSTRACT

The nondestructive detection and characterization of crystal defects in monocrystalline semiconductor material is by a combination of photoluminescence heterodyne spectroscopy, photothermal heterodyne spectroscopy and SIRD.

7 Claims, 2 Drawing Sheets

METHOD AND DEVICE FOR NONDESTRUCTIVE DETECTION OF CRYSTAL DEFECTS

BACKGROUND OF THE INVENTION

1. Field of the Invention

The present invention relates to a method for nondestructive detection and characterization of crystal defects in monocrystalline semiconductor material, and to a device for detecting and characterizing crystal defects.

2. The Prior Art

In order to be suitable for further processing for making components or integrated circuits, monocrystalline semiconductor material, for example silicon material, must meet certain requirements. Consequently, material exhibiting crystal defects, for example dislocations, must be detected, characterized and removed.

Within the scope of the invention, the term "detection" is intended to mean the identification of regions in monocrystalline semiconductor material which suffer from crystal defects. The term "characterization" is intended to mean the allocation of these crystal defects to a defect group.

Growth-related crystal defects actually occur during the formation of monocrystalline semiconductor material. It is, however, also possible for crystal defects not to be generated until the subsequent production of the semiconductor wafers or the components. In this case, they are referred to as process-induced crystal defects. Crystal defects may occur both on the surface of the specimen and inside the specimen.

The nomenclature for crystal defects is in accordance with the standards from DIN (Deutsches Institut für Normung e.V.) and ASTM (American Society for Testing Materials, 1916 Race St., Philadelphia, Pa. 19103). The documents DIN 50434 and ASTM F1241-93, D93-3/4, F154-88, F416-75 and F416-88 are particularly relevant.

Examples of crystal defects which, in particular, can be detected in a silicon crystal rod include dislocations, stacking faults and point defect aggregates. In the silicon wafer, defects which can be detected include cracks and eruptions. Particularly in the wafer edge region, defects caused by holding tools, for example scratches, can be detected. Defects developed by heat treatments, such as dislocations and stacking faults, can also be detected.

In the prior art, crystal defects in monocrystalline semiconductor material are examined, for example, by defect etching. This involves preferentially acting chemical etching. In this case, one component of the etch solution, for example $HNO_3$, oxidizes the semiconductor material, a second, for example HF, dissolves the oxide and another, for example $CH_3COOH$, controls the etching rate by acting as a kind of diluent. The oxidation in the vicinity of a crystal defect takes place in a different way than does the oxidation of perfectly crystalline surroundings. This difference is then examined, for example, using an optical reflected-light microscope. Using this method, it is possible to detect and characterize crystal defects which are detrimental to semiconductor applications.

All defect etching methods change the specimen material, both chemically and morphologically, and thus have a destructive effect. The specimen material needs to be cut beforehand from the rod-shaped single crystal in the form of thin test wafers.

Using other prior art methods, for example electrical resistance measurement, it is likewise possible to detect a modified material property in the region of crystal defects. In relation to the surroundings with unperturbed crystallinity, a signal contrast is measured in this case but without the possibility of characterizing the crystal defect. The characterization is achieved only after further investigations, for example by defect etching (cf. *VLSI Electronics, Microstructure Science* Vol. 12, *Silicon Materials*' Academic Press, 1985).

Other alternative prior art methods, for example X-ray topography, can only be implemented with complicated equipment and by spending a great deal of time. These prior art methods have only limited suitability for control carried out on a production line.

For determining the electrical parameters of a semiconductor, EP 0 735 378 A2 has described the measurement principle of photothermal heterodyne spectroscopy (PTH spectroscopy) in combination with photoluminescence heterodyne spectroscopy (PLH spectroscopy).

The PTH method is based on depositing energy in a specimen to be examined, by absorption of intensity-modulated laser light in defined ranges at two modulation frequencies. In the specimen, a temperature wave (heat wave) is produced, and in semiconductors a charge-carrier wave is produced in addition. The amplitude and the phase of the wave depend on the physical properties of the specimen. The two response waves are optically detected in the reflection of the stimulated laser light. This is through the antiphase modulation of the dielectric properties of the semiconductor which they cause, and are measured with phase resolution. The value measured is the conversion coefficient K. This K indicates the fraction of the laser power which, in proportion to the laser power density absorbed in the object to be measured, is converted to the differential frequency by interaction with the object to be measured.

The PTL method is based on a response measurement method which is operated in the frequency domain and which tracks the relaxation of nonequilibrium charge carriers by time-resolved band-band luminescence radiation. The value measured is the normalized conversion efficiency of the luminance output L. PTH/PLH spectroscopy as such does not allow actual characterization of the crystal defects.

*J. Appl. Phys.* 30, (1959) 1631 reports that crystal defects induce optical birefringences which are detected by the SIRD method (SIRD—scanning infrared depolarization). This method was first used by Lundt et al. as an evaluation method in silicon wafer production (H. Lundt, M. Kerstan and R. Weiss, *Proc. of the Spring Topical Meeting of the American Society for Precision Engineering*, 42, Tucson 1993). It is not, however, possible for individual crystal defects to be detected and characterized using the SIRD method.

Some of the methods and devices for detecting and characterizing crystal defects in monocrystalline semiconductor material according to the prior art do not work nondestructively e.g. preferentially etching, while others can only be implemented with a high outlay on equipment and safety (e.g. x-ray, topography). For the time and position measurements independent of a production line, which are, furthermore, time-consuming, special test wafers need to be prepared in each case. In view of the increasing wafer diameter of silicon wafers, these test wafers represent an ever more expensive starting material for this type of analysis, especially when the absence of defects has been confirmed. Further, the aforementioned methods, as individual methods, and the devices mentioned are not suitable for controlling a mass-produced product, such as silicon wafers on a production line.

SUMMARY OF THE INVENTION

It is an object of the present invention to provide a method and a device which allow rapid nondestructive detection of crystal defects on monocrystalline silicon material, for example silicon wafers or silicon rods. A further object of the invention is to characterize the crystal defects.

These objects are achieved by methods for detecting and characterizing crystal defects in monocrystalline semiconductor material by means of photoluminescence heterodyne spectroscopy, photothermal heterodyne spectroscopy and SIRD methods, wherein the detection and characterization is carried out by a combination of these measurement methods. These objects are also achieved by a device for carrying out these measurements.

No one of the aforementioned measurement methods is entirely suitable for the reliable characterization of crystal defects. Conversely, the combination, according to the invention, of the measurement methods, in the form of the device of the invention, permits not only reliable detection but also reliable characterization of the crystal defects as well.

For example, the value of the magnitude of the conversion coefficient K in the PTH spectroscopy is used for the characterization of crystal defects. The justification for this is that it has been found that there is a relationship between the conversion coefficient and the degree of crystalline integrity. The conversion coefficient in the region perturbed, for example, by dislocations is greater than in a perfectly crystalline region.

According to the invention, the value of the magnitude of the luminescence output L in the PLH spectroscopy is used for the detection of crystal defects. The justification for this is that it has been found that the luminescence output in the vicinity of crystal defects is different from that in the region with perfect crystallinity. The value of the magnitude of the luminescence yield, for example in the vicinity of dislocations, is less than in a perfectly crystalline region.

According to the invention, the change in the degree of depolarization when applied in the SIRD method is used for the characterization of crystal defects. For example, the degree of depolarization increases in the vicinity of dislocations compared with a perfect crystal region.

The SIRD method, in combination with PTH and PLH spectroscopy, allows for the reliable detection and characterization of crystal defects.

The device for carrying out the method of the invention has a PTH and PLH spectrometer and an SIRD module. It may also be equipped with an optical measurement and detection device, for example with a reflected-light microscope.

It has further been found that nondestructive detection of crystal defects on monocrystalline silicon single crystals is possible if the material is, as a result of heteronucleation, for example decorated by Cristobalite. By using a reflected-light microscope it is thus possible to readily detect and characterize dislocations in silicon material pulled from a crucible.

With the method according to the invention and the device for carrying out the method, it is no longer necessary to produce, process and subsequently assess specially prepared semiconductor material, for example silicon test wafers. It is not necessary to dispose of toxic processing media, for example chromic acids. The claimed method can be applied to any type of monocrystalline semiconductor material. Thus it can therefore be integrated at any desired point into a fabrication line for silicon wafers. The automated detection, storage and evaluation of the measurements can be by a process computer. This makes it possible for assessment of the material to take place in the production line after each of the individual processing steps.

BRIEF DESCRIPTION OF THE DRAWINGS

Other objects and features of the present invention will become apparent from the following detailed description considered in connection with the accompanying drawings which disclose several embodiments of the present invention. It should be understood, however, that the drawings are designed for the purpose of illustration only and not as a definition of the limits of the invention.

In the drawing, wherein similar reference characters denote similar elements throughout the several views:

FIG. 1b shows a PTH survey image of a region of the wafer of FIG. 1a;

FIG. 1c shows an increase in the magnitude of the PTH conversion coefficient K at the pertinent points of the wafer of FIG. 1a.

DETAILED DESCRIPTION OF PREFERRED EMBODIMENTS

Figure 1A:
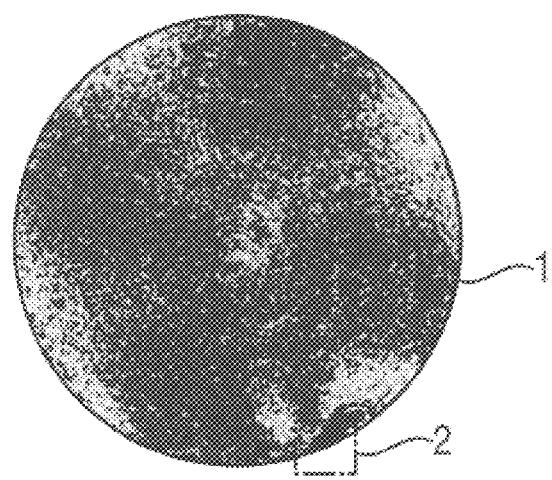
FIG. 1a shows a silicon wafer which has been sampled surface-wide using the SIRD method.
Figure 1B:
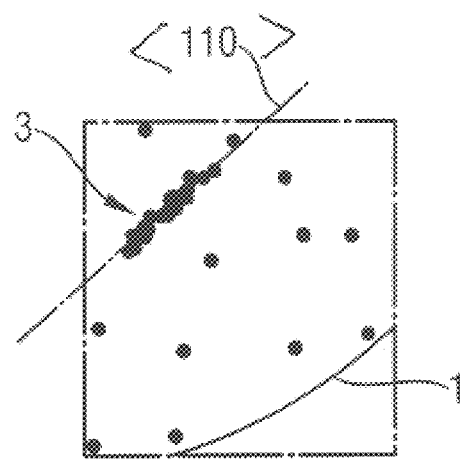
Figure 1C:
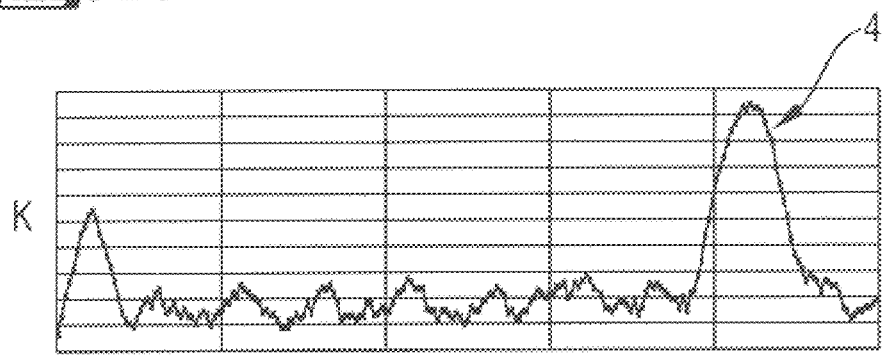

Turning now in detail to the drawings, FIGS. 1a to 1c show the detection and characterization of a crystal defect in a silicon wafer, by combining the SIRD and PTH measurement methods. The example of the detection and characterization is intended to illustrate the invention, but does not restrict its scope. Any other combination of the measurement methods is possible.

FIG. 1a shows a silicon wafer 1 which has been sampled surface-wide using the SIRD method. In the SIRD survey image, the SIRD signal deviates from the surroundings at a location 2 at the edge of the wafer.

A subsequent two-dimensional PTH analysis of this region shows spot deviations in the PTH signal from the reference. FIG. 1b shows a PTH survey image of 2. Some of these deviations are arranged in a line 3; the lines run in the <110> crystallographic direction.

High-resolution PTH analysis in linescan mode (FIG. 1c) shows an increase in the magnitude of the PTH conversion coefficient K at the pertinent points 4. This combination of features includes a modified SIRD signal, an increase in the magnitude of the PTH conversion coefficient K and the sometimes linear sequencing of these results in the <110> crystallographic direction. This combination implies that the crystal defect to be characterized involves dislocations arranged in a line.

Figure 2:
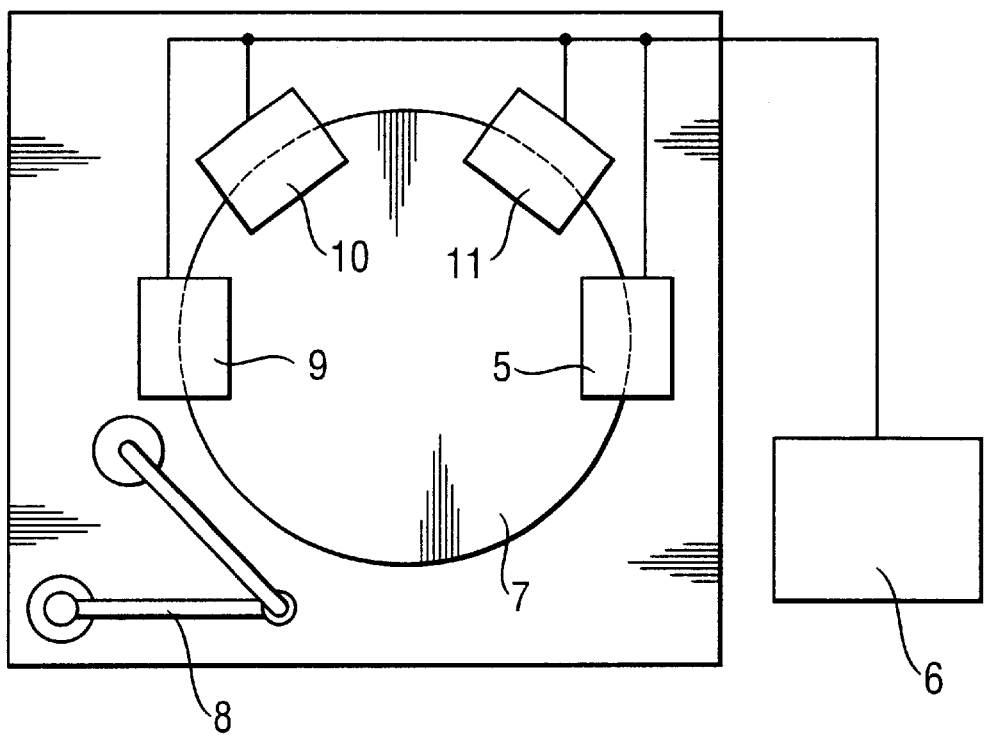
FIG. 2 shows in one device a combination of the individual means which are useful for implementing the method according to the invention.

FIG. 2 shows in one device a combination of the individual means which make it possible to implement the method according to the invention.

Monocrystalline semiconductor material 7 is automatically transferred, for example by a holding and transport device 8, into a position suitable for the examination. A PLH spectrometer 9, a PTH spectrometer 10 and an SIRD module 11 as well as a reflected-light microscope 5 are arranged over the specimen to be examined. The individual measurement methods are then applied successively or at the same time to the specimen 7 to be examined. All or a selection of the measurement methods may in this case be employed. The measurements, which are meaningful only when in combination, dictate whether the material is to be processed further or discarded. Computer-assisted analysis of the measurements and the comparison of the data obtained in this way with the data in a defect database also proves to be helpful.

In particular, the examination of crystal rods is carried out with the optical system 5, since dislocations are detected rapidly and reliably on the lateral surface of the rod. The measurements are stored in a process computer 6. The specimen 7 is removed from the measurement device by the holding and transport device 8.

Depending on the point on the fabrication line at which the device is integrated, the specimen examined may be raw material, for example silicon rods. Also, the specimen examined may be already processed material, for example silicon wafers with rounded edges. The method may also be applied to electronic devices.

Accordingly, while a few embodiments of the present invention have been shown and described, it is to be understood that many changes and modifications may be made thereunto without departing from the spirit and scope of the invention as defined in the appended claims.

What is claimed is:

1. A method for detecting and characterizing crystal defects in monocrystalline semiconductor material comprising providing monocrystalline semiconductor material to be examined; and examining said material by utilizing a combination of at least two means selected from the group consisting of photoluminescence heterodyne spectroscopy, photothermal heterodyne spectroscopy and SIRD measurement methods.

2. The method as claimed in claim 1, wherein the characterizing of crystal defects is carried out using measurement results which are obtained from the combination of measurement methods.

3. The method as claimed in claim 1, further comprising using an optical reflected-light microscope, whereby dislocations are characterized and detected by decoration with Cristobalite.

4. The method as claimed in claim 1, comprising examining said semiconductor material after each individual processing step in a fabrication line for producing silicon single crystals and silicon wafers.

5. The method as claimed in claim 1, further comprising providing computer-assisted analysis of measurements; and comparing data obtained by said analysis with data in a defect database, such that said data can be further evaluated by said process computer.

6. A device for detecting and characterizing crystal defects in monocrystalline semiconductor material, comprising a photoluminescence heterodyne spectrometer, a photothermal heterodyne spectrometer, an SIRD module and an optical measurement and detection device.

7. The device as claimed in claim 6, further comprising a holding and transport device; and a process computer.

* * * * *